United States Patent [19]

Wang et al.

[11] Patent Number: 5,799,099
[45] Date of Patent: Aug. 25, 1998

[54] AUTOMATIC TECHNIQUE FOR LOCALIZING EXTERNALLY ATTACHED FIDUCIAL MARKERS IN VOLUME IMAGES OF THE HEAD

[75] Inventors: Matthew Y. Wang; Calvin R. Maurer, Jr.; J. Michael Fitzpatrick, all of Nashville, Tenn.

[73] Assignee: George S. Allen, Nashville, Tenn.

[21] Appl. No.: 471,456

[22] Filed: Jun. 6, 1995

Related U.S. Application Data

[60] Division of Ser. No. 196,725, Feb. 15, 1994, abandoned, which is a continuation-in-part of Ser. No. 164,933, Dec. 10, 1993, abandoned, and Ser. No. 17,167, Feb. 12, 1993, abandoned, and Ser. No. 162,986, Dec. 8, 1993, abandoned.

[51] Int. Cl.⁶ .................. G06K 9/00; G06K 9/36
[52] U.S. Cl. ............. 382/131; 382/154; 382/291; 600/426
[58] Field of Search ........................ 382/288, 291, 382/154, 131, 201, 170, 308, 260, 262, 254; 128/653.1, 653.2, 653.4; 364/413.13, 413.14, 413.15; 378/162–164, 204, 205; 600/426, 425

[56] References Cited

U.S. PATENT DOCUMENTS

| | | | |
|---|---|---|---|
| 4,322,716 | 3/1982 | Sternberg | 340/146.3 |
| 4,341,220 | 7/1982 | Perry | 128/630 |
| 4,475,122 | 10/1984 | Green | 358/101 |
| 4,572,198 | 2/1986 | Codrington | 128/653 |
| 4,583,538 | 4/1986 | Onik et al. | 128/303 B |
| 4,665,554 | 5/1987 | Sternberg | 382/205 |
| 4,922,915 | 5/1990 | Arnold et al. | 128/653 R |
| 4,945,914 | 8/1990 | Allen | 128/653 R |
| 4,948,955 | 8/1990 | Lee et al. | 235/462 |
| 4,991,579 | 2/1991 | Allen | 128/653 R |
| 5,003,979 | 4/1991 | Merickel et al. | 128/653 A |
| 5,005,578 | 4/1991 | Greer et al. | 128/653 A |
| 5,115,813 | 5/1992 | Ylander et al. | 128/660.01 |
| 5,129,014 | 7/1992 | Bloomberg | 382/282 |
| 5,142,930 | 9/1992 | Allen et al. | 74/469 |
| 5,186,174 | 2/1993 | Schlöndorff et al. | 128/653.1 |

(List continued on next page.)

OTHER PUBLICATIONS

Wang, Matthew Y., Maurer, Jr., Calvin R., Fitzpatrick, J. Michael, Maciunas, Robert J., "A Knowledge–Based Technique for Localizing Externally Attached Markers in MR and CT Volume Images of the Head", Proceedings of the Annual International Conference of the IEEE Engineering in Medicine and Biology Society, vol. 15, Oct. 28–31, 1993, pp. 120–121.

Maurer, Jr., Calvin R., Fitzpatrick, J. Michael, Wang, Matthew Y., Maciunas, Robert J., "Estimation of Localization Accuracy for Markers in Multimodal Volume Images", Proceedings of the Annual International Conference of the IEEE Engineering in Medicine and Biology Society, Oct. 28–31, 1993, pp. 124–125.

(List continued on next page.)

Primary Examiner—Yon J. Couso
Assistant Examiner—Ha Tran Nguyen
Attorney, Agent, or Firm—Kenyon & Kenyon

[57] ABSTRACT

An automatic computer implemented technique which may be used for identifying markers and determining the centroids of fiducial markers (e.g., cylindrical fiducial markers) attached to the head in magnetic resonance (MR) and X-ray computed tomography (CT) volume images is disclosed. This technique may be referred to as image space localization. A first portion of the technique identifies many candidate voxel points included in a bright area of the image which may correspond to candidate markers. A second portion of the technique selects from the identified candidate voxels a predetermined number of candidate points of the image volume that are most likely to lie within an actual fiducial marker. The centroid for each of these markers is then determined. The method finds markers whose images are of a higher intensity than their surroundings and which have a given shape and size.

6 Claims, 6 Drawing Sheets

U.S. PATENT DOCUMENTS

| | | | |
|---|---|---|---|
| 5,197,476 | 3/1993 | Nowacki et al. | 128/660.03 |
| 5,205,289 | 4/1993 | Hardy et al. | 128/653.1 |
| 5,230,338 | 7/1993 | Allen et al. | 128/653 |
| 5,347,588 | 9/1994 | Wilson | 382/100 |
| 5,365,996 | 11/1994 | Crook | 164/45 |
| 5,397,329 | 3/1995 | Allen | 606/73 |
| 5,564,412 | 10/1996 | Hennig | 128/653.2 |

OTHER PUBLICATIONS

Maurer, Calvin R., Jr., Fitzpatrick, J. Michael, Wang, Matthew Y., Maciunas, Robert J., "Correction of Geometrical Distortion in MR Image Registration", Proceedings of the Annual International Conference of the IEEE Engineering in Medicine and Biology Society, Oct. 28–31, 1993, pp. 122–123.

Mandava, Venkat R., Fitzpatrick, J. Michael, Maurer, Jr., Calvin R., Maciunas, Robert J., Allen, George S., "Registration of Multimodal Volume Head Images Via Attached Markers", Medical Imaging VI: Image Processing Proc. SPIE 1652; Feb. 20, 1992, pp. 271–282.

Haralick, Robert M., Shapiro, Linda G., *Computer and Robot Vision*, vol. I, pp. 14–29, Feb. 13, 1992.

Dougherty, Edward R., *An Introduction to Morphological Image Processing*, 1992, pp. 1–30.

Mandava, Venkateswara Rao, *Three Dimensional Multimodel Image Registration Using Implanted Markers* (PhD Dissertation), Dec. 1991, pp. 16–58.

Gonzalez, Rafael C., Woods, Richard E., *Digital Image Processing*, pp. 191–192.

Maurer, Jr., Calvin R., Fitzpatrick, J. Michael, "A Review of Medical Image Registration", *Interactive Image–Guided Neurosurgery*, 1993, pp. 17–44.

AUTOMATIC TECHNIQUE FOR LOCALIZING EXTERNALLY ATTACHED FIDUCIAL MARKERS IN VOLUME IMAGES OF THE HEAD

DISCUSSION OF RELATED APPLICATIONS

This is a division application of U.S. patent application Ser. No. 08/196,725 filed on Feb. 15, 1994, now abn., which is a continuation-in-part application of U.S. patent application Ser. No. 08/164,933 filed on Dec. 10, 1993, now abandoned, which is incorporated herein by reference. This is also a continuation-in-part application of U.S. patent application Ser. No. 08/017,167 filed on Feb. 12, 1993, now abandoned, which is also incorporated herein by reference. Further, this is a continuation-in-part application of U.S. patent application Ser. No. 08/162,986 filed on Dec. 8, 1993, now abandoned, which is incorporated herein by reference.

BACKGROUND OF THE INVENTION

The present invention relates to a method of finding the image positions of three or more "fiducial markers", which are small objects that show up as small bright spots in images such as, for example, computed tomography (CT) and magnetic resonance (MR) images. This process of finding positions of fiducial markers in an image is also referred to as image space localization.

The images discussed above are "volume" images, meaning that they are sets of contiguous slices that span a volume of space. They are acquired by placing the patient into a CT scanner or an MR scanner. One or both of these imaging modalities or any other such imaging modality may be used for a given patient for a given surgery.

Different imaging modalities provide different types of information that can be combined to aid diagnosis and surgery. Bone, for example, is seen best on x-ray computed tomography (CT) images, while soft-tissue structures are best seen by magnetic resonance imaging (MRI). Because of the complementary nature of the information in these two imaging modalities, the registration of MR images of the head with CT images is of growing importance for diagnosis and for surgical planning. Furthermore, for the purpose of navigation during surgery it is helpful to be able to register images to the patient anatomy itself. Registration is defined herein as the determination of a one-to-one mapping between the coordinates in one space and those of another, such that points in the two spaces that correspond to the same anatomic point are mapped to each other.

U.S. Pat. No. 4,945,914, U.S. Pat. No. 4,991,579, U.S. Pat. No. 5,142,930, and U.S. Pat. No. 5,230,338 disclose a method for utilizing fiducial markers to establish a coordinate system that facilitates the registration of image spaces and physical spaces across time. The contents of U.S. Pat. No. 4,945,914, U.S. Pat. No. 4,991,579, U.S. Pat. No. 5,142,930 and U.S. Pat. No. 5,230,338 are incorporated herein by reference.

Briefly, these patents disclose using temporary or permanent markers that are imageable in the image space produced by a scanner. The markers may be attached to the skull via small posts that pierce the scalp and screw into the bone. The markers may also be attached by first drilling a hole and then inserting via a self-tapping thread a base into the hole, to which a temporary marker is subsequently attached. In any case, since the posts or bases are physically attached to the skull, the markers are referred to as "implanted" markers. Further, the markers are referred to as "external" markers, since the part of the marker that produces the bright spot in the image is outside the head.

In order to make full use of markers, they must be localized in the image space of the scan in question. Previous techniques have related to calling up successive images and manually locating spots whose brightness would appear to be indicative of the presence of a marker. However, this is an error prone, time consuming and labor intensive process. Therefore, there remains a need for the further development of more automated techniques for localizing markers in images such as MR and CT volume images.

SUMMARY OF THE INVENTION

Broadly speaking, the present invention uses a computerized program of operation to fully and automatically locate and localize attached markers in an image volume. The image volume is first searched for "seed points", which are candidate voxels that lie within candidate (i.e., potential) markers. Next, the region around each candidate voxel (in the original image) is examined to discard false positives from the set of candidate voxels and to determine their centroids more precisely.

The present invention relates to an automatic technique for finding the centroids of fiducial markers attached to the head in, for example, magnetic resonance (MR) or X-ray computed tomography (CT) volume images, or images of any other imaging modality. A marker's centroid is referred to as its "fiducial point". These fiducial points are used, for example, to register MR images with CT images.

The fiducial markers found using the technique of the present invention may be of any size or shape. However, in a preferred embodiment of the present invention, the fiducial markers are cylindrical fiducial markers.

The localization technique according to the present invention is fast, automatic, and knowledge-based, and includes two major portions. The first part of the method according to the present invention searches the entire image volume for candidate voxels that lie within candidate markers. It is preferred that the dimensions of the marker (e.g., the inside height h and diameter d of a cylindrical fiducial marker) and the three dimensions of the voxels that make up the image are known, that the intensity of the marker is higher than its surroundings, and that its image consists of one connected component. First, noise reduction via median filtering is applied if the image is an MR image, and the volume is subsampled to reduce subsequent computation. A binary image is then formed in which voxels whose intensities are similar to air are set to background. For MR, in order to remove spurious detail from within the head, any background pixels recursively not connected within the slice to the edge of the image are set to foreground.

A morphological opening, which is a nonlinear operation on binary images that causes changes in the shape of the foreground objects, is performed on the brighter components using an element slightly larger than a marker to remove small objects (including markers). The morphological opening is followed by a morphological dilation using a smallest possible element that consists of, for example, one voxel. Morphological dilation includes complementing the image by setting all foreground information to background and all background information to foreground, rotating the image 180 degrees, performing a morphological erosion, and complementing the resulting image. A morphological erosion includes placing a structuring element successively at all possible positions within an image, noting the center pixel of the element when the entire element lies within the foreground, and generating a new image in which each noted position is set to foreground and other positions are set to background. Alternatively, an erosion may be performed with an element approximately equal in size to a marker followed by a dilation with an element slightly bigger than the erosion element. A three dimensional connected-components labeling is executed on the objects that were removed by the morphological opening. Finally, the centroid of each connected component is determined. Each such centroid serves as a candidate voxel.

The second part of the method according to the present invention examines the region around each candidate voxel (in the original image) to discard false positives from the first part of the method and to determine their centroids more precisely. First, a local threshold is determined to segment the voxels within a spherical region of radius R equal to the greatest straight-line distance between any pair of points on the marker and centered on the candidate voxel. For example, for a cylindrical marker of height h and diameter d, the radius $R=(h^2+d^2)^{1/2}$. The determination of the threshold is accomplished through a knowledge-based search as follows. S(t) is defined as the set of voxels in this region whose intensity i is greater than the threshold t and which are connected recursively (in 3-D) to the starting point. V(t) is defined as the volume of the set of voxels S(t), and $V_h$ is the maximum volume and $V_l$ is the minimum volume that are allowed for a marker image. The method according to the present invention first searches for the smallest t such that no voxel included in the set of voxels S(t) is farther than R from the starting point. If $V(t)>V_h$, t is increased until $V(t)=V_h$. If $V(t)<V_l$, the segmentation fails and the candidate voxel is discarded. If the segmentation succeeds, the fiducial point f is calculated on the basis of the final threshold $t_f$ as $f=\Sigma(i-i_0)r/\Sigma(i-i_0)$, where the sum is taken over all voxels in $S(t_f)$, $i_0$ is the intensity of an empty voxel, and r is the three dimensional position vector of a voxel.

After these two major parts of the method of the present invention are implemented, the fiducial points localized in the image volume are ranked according to the average intensity of the marker voxels from brightest to darkest. The n brightest marker voxels, where n is the number of markers known to be present in the volume, are declared to be fiducial points. Thus the number of false positives is less than or equal to the number of false negatives.

BRIEF DESCRIPTION OF THE DRAWINGS

Other features and advantages of the present invention will become apparent from the following description taken in conjunction with the attached drawings, wherein.

DETAILED DESCRIPTION

Figure 1:
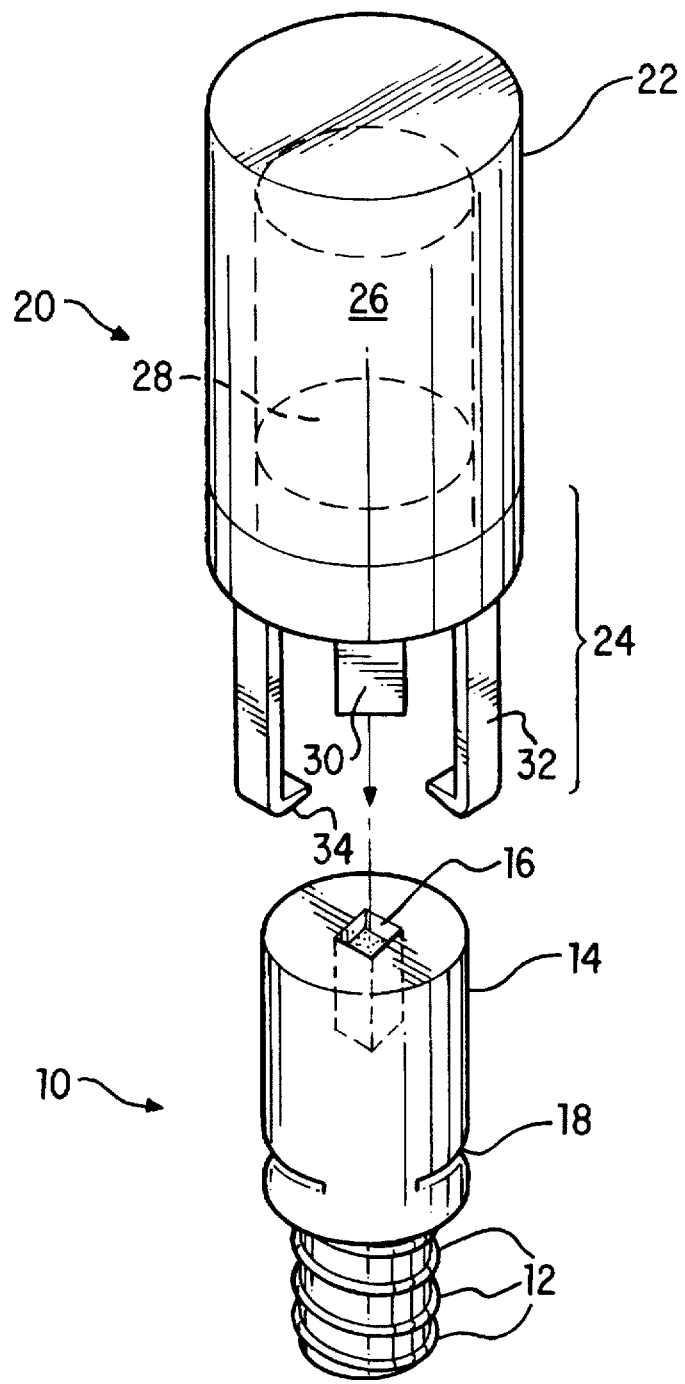
FIG. 1 illustrates a temporary fiducial marker assembly which may be used in implementing an embodiment of the present invention.

Referring now specifically to the drawings, FIG. 1 illustrates a temporary fiducial marker assembly which may be used in implementing an embodiment of the present invention. The temporary fiducial marker assembly illustrated in FIG. 1 includes a base 10 and an imaging marker 20.

The base 10 has a threaded portion 12 at a first end. The threads 12 enable a surgeon to securely attach the base 10 into the skull or other desired portion of bone tissue of a patient. Other connecting structure is provided to securely and releasibly link the imaging marker 20 with the base 10. For example, in the illustrated embodiment, the end of the base 10 opposite the threaded portion 12 terminates in a socket head 14 which contains a socket-like recess 16. (It is anticipated that the base would be implanted into bone with the aid of an insertion tool that twists the base into the bone or into a hole provided in the bone. The recess is non-circular so as to better transmit the torque provided by such an insertion tool.) Just beneath the socket head 14 are a plurality of grooves 18 (i.e., three grooves around the circumference of the base portion 10). As shall be further explained below, the socket 14 and the grooves 18 provide for the secure and releasable attachment of the imaging marker portion 20 with base portion 10.

The imaging marker portion 20 of the temporary fiducial marker assembly may consist of two principal portions, a cylinder 22 and a cap 24. The cylinder 22 contains a cavity 26 (shown by dotted lines in FIG. 1) for receiving a mixture of imaging agents whose composition is determined by the imaging modalities to be employed. While in this version, the vessel containing the imaging agents is preferably cylindrical to simplify the process by which the centroid of the corresponding volume of imaging agent is determined, other shapes (such as a box or sphere) could be employed as well. The cylinder 22 is closed at one end and open at the other end to allow for the introduction of the imaging agents. In one version of the device, a cap 24 is used to seal off the open end of the cylinder 22 once the imaging agents have been added to the cylinder. In this version, the cap may be cemented or welded into place. The cap may be provided with a plug portion 28 that protrudes into and thereby helps seal off the cavity 26 of the cylinder 22 against leakage of the imaging agents. Other conventional filling and sealing techniques, such as blow-molding, ultrasonic welding, or heat sealing, may be used.

Where a cap is employed, it may be provided with a protruding boss 30 and a plurality (e.g., three) of snap arms 32, which terminate with inwardly projecting portions 34. The shape and dimensions of the boss 30 are in direct correspondence with the shape and size of the socket 16 provided in the base 10 to properly and securely center the imaging marker on the base. The snap arms 32 cooperate with the grooves 18 of the base 10 to detachably secure the imaging marker onto the base. While this example shows the use of snap arms, other fastener structures may be provided for attaching the marker to the base (e.g., screw threads, clasps, hooks, etc.).

The dimensions of the temporary fiducial marker assembly will be somewhat dependent on the state of the art of imaging. The greater the sensitivity of the scanner employed, the lesser the quantity of imaging material necessary to provide a suitable image, which in turn makes it possible to reduce the corresponding size of the marker that must be employed to contain the imaging material. The fiducial marker assembly including a base portion approximately 12 mm in length and 2 mm–3 mm in diameter is sufficiently large to provide for the secure placement of the base into the bone beneath the skin. When the clinician prepares the patient for imaging, the base portion is exposed and an imaging marker approximately 6 mm in length is attached to the base; the marker itself may protrude from the scalp and be exposed to air while a scan is performed on the patient. The base and the imaging marker housing are constructed of a bio-compatible organic polymer, such as polyether imide.

While an example of a fiducial marker which may be used in implementing the present invention has been described as set forth above, it is noted that the present invention is not limited to such a fiducial marker. For example, the fiducial marker used in implementing the present invention need not necessarily be a cylindrical fiducial marker. Any fiducial marker may be used in implementing the present invention which is imageable in an image space produced by a scanner such as, for example, a magnetic resonance (MR) or computer tomography (CT) scanner.

In order to practice the present invention, a three-dimensional internal coordinate system must be set up which is fixed within a human anatomy. The internal coordinate system is established within the anatomy by fixing three or more fiducial implants (i.e., fiducial markers) to portions of the anatomy. The fiducial markers are fixed to points which will not change their spacial relationship to one another over a relatively long period of time, such as a few months or more.

Figure 2B:
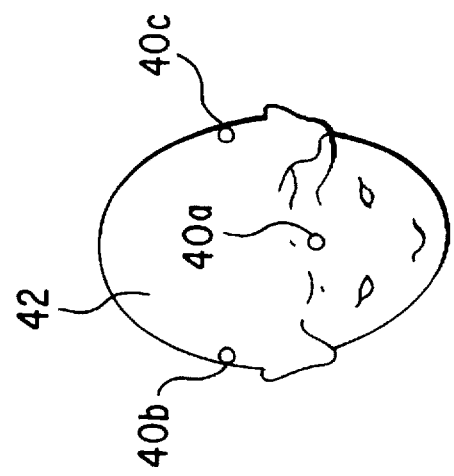
FIG. 2A and FIG. 2B illustrate an example of the placement of fiducial implants in the anatomy which may be localized using the method of the present invention.
Figure 2A:
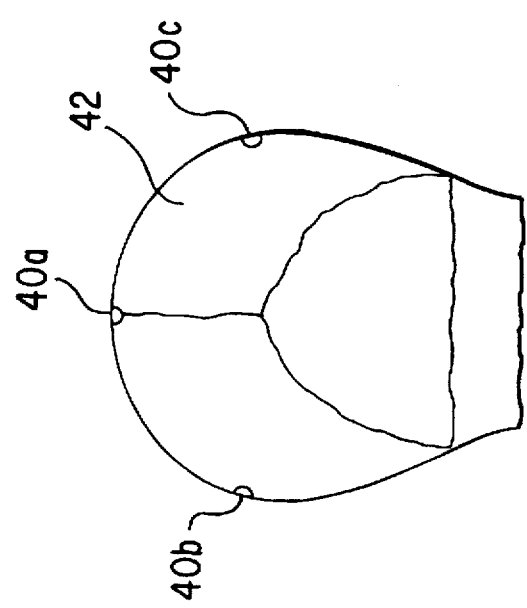

An example of placement of fiducial implants in the anatomy is shown in FIG. 2A and FIG. 2B. In these figures, fiducial implants 40a, 40b and 40c are implanted in three separate, spaced locations within the skull 42 of a patient.

Since these three fiducial implants 40a, 40b and 40c are arranged in a noncollinear manner, a plane is formed which contains these fiducial markers 40a, 40b and 40c. Once a plane is defined, a three-dimensional coordinate system is defined. Any point within the body will be within the internal coordinate system.

Although fiducial implants are shown, any three points that are affixed with respect to the region of interest can comprise the three points used to define the internal coordinate system. However, fiducial implants 40a, 40b and 40c that are identifiable and measurable by different imaging systems, such as CT imagers and MR imagers are preferred. As described above, the fiducial markers 40a, 40b and 40c may be relatively small and unobtrusive so that no discomfort or self consciousness will be experienced by the patient even though the patient may carry the implants for a relatively long period of time.

A number M of markers are attached to the patient's head before images of the head are acquired (M is equal to 3 in FIG. 2A and FIG. 2B). The markers are left in place during the imaging and are not removed until after the completion of the surgical procedure that follows the imaging.

Figure 3:
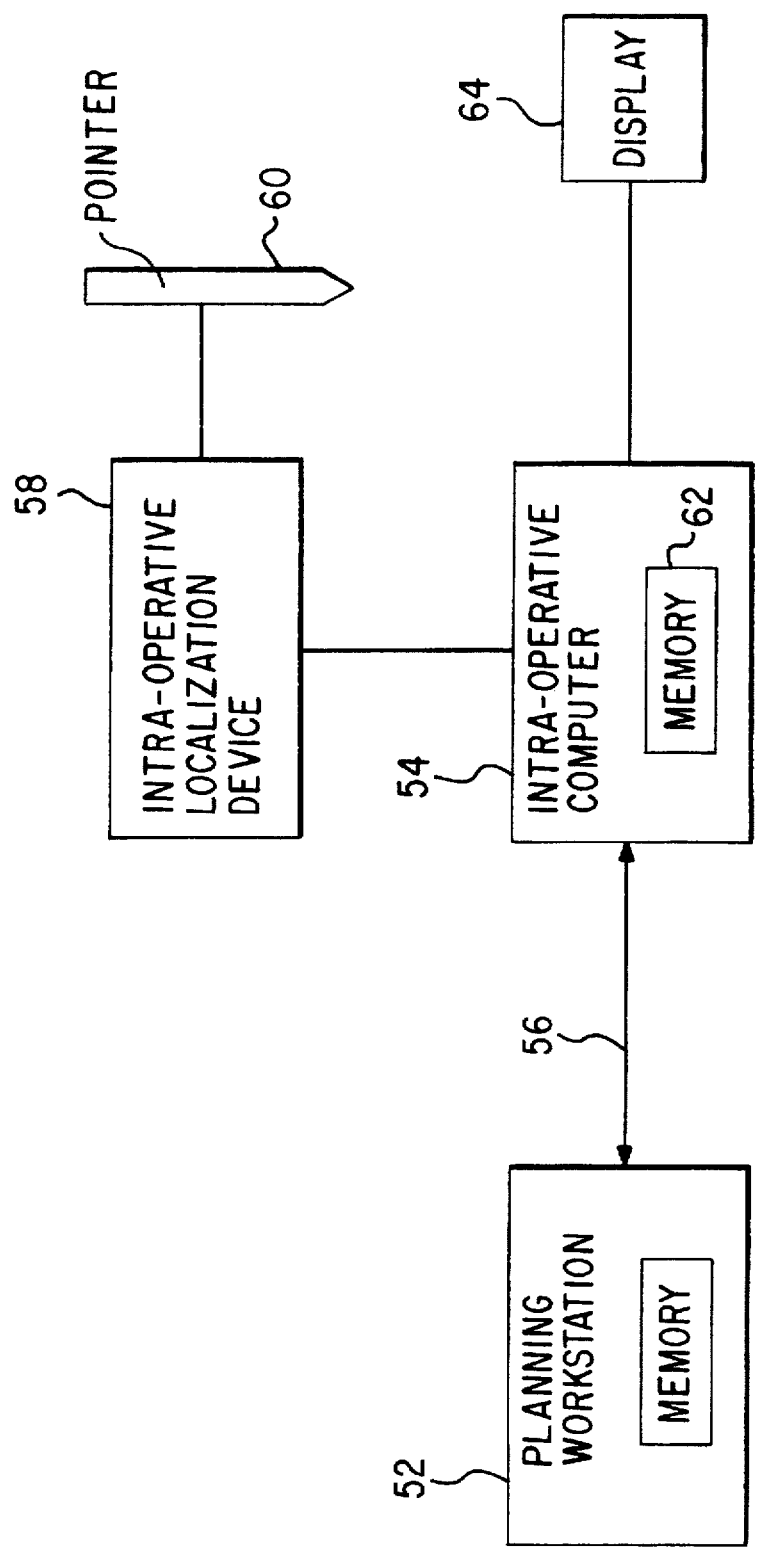
FIG. 3 illustrates an imaging system which may be used in implementing an embodiment of the present invention.

FIG. 3 illustrates an imaging system which may be used in implementing an embodiment of the present invention. Additional details of such an imaging system are included in U.S. patent application Ser. No. 08/162,986 filed on Dec. 8, 1993 and which has been incorporated herein by reference. After imaging, but before the surgery, the images are loaded into the memory of a computer 52 illustrated in FIG. 3, which is referred to as the "planning workstation" and a method is executed by the planning workstation computer 52 to find the position of each of the markers within each of the images. The term "planning workstation" relates to the fact that the computer 52 provides additional programs that the surgeon may use to plan the surgical approach to be used on the patient. Because the volume image is three dimensional, the specification of a position requires three coordinates, typically referred to as x, y, and z. At this point, the method of the present invention is implemented to provide image space localization of the markers in the image space.

The marker positions, which we call the "positions in image space" or "image space positions", are transferred from the planning workstation 52 to a computer 54 located in the operating room, which is referred to as the "intra-operative computer". This transfer of the marker positions may be accomplished by means of a diskette, optical disk or tape, etc. which is written by the planning workstation and read by the intra-operative computer, or by means of a network connection 56 between the planning workstation and the intra-operative computer. If N volume images are acquired, there will be M×N positions transferred from the planning workstation 52 to the intra-operative computer 54, one for each marker and each volume image, or 3×M×N coordinates, since three coordinates are required for each position. In addition, some or all of the N volume images of the patient may be transferred from the planning workstation 52 to the intra-operative computer 54.

In the operating room, after the patient's head has been securely fastened to the operating table in the standard manner and before the surgery begins, the physical positions of the markers are measured. These physical positions are referred to as the "positions in physical space" or "physical space positions". The measurement of a physical position is referred to as "physical space localization". Physical space localization is accomplished with a precision instrument such as an "intra-operative localization device" (or ILD) 58 that is connected to the intra-operative computer 54. The ILD 58 employs a hand-held wand (or pointer) 60 with which the surgeon touches each marker. The ILD is able to determine the position of the tip of the pointer 60 at any time. When the surgeon has positioned the wand 60 so that it is touching a marker, the surgeon presses a button that causes the intra-operative computer 54 to write that position into its memory 62. The process of measuring the physical positions of the markers is completed by touching each of the M markers with the wand 60 and recording its position in the memory 62 of the intra-operative computer 54.

The exact position of each of the markers may be established, for example, by providing a divot (not illustrated) formed in the top of the cylinder 12 of the imaging marker portion 10 of the fiducial marker assembly. The tip of the pointer 60 of the ILD 58 may then be accommodated within the divot so that an exact position of the marker is established.

At this point two or more separate sets of coordinates are stored in the intra-operative computer: one set of 3×M physical space coordinates and N sets of 3×M image space coordinates, where M is the number of markers and N is the number of images stored in the planning workstation computer 52. Two sets of coordinates will almost never be the same, because the orientation of the head relative to the image scanners will almost always differ from each other and from the ILD. However, by comparing the set of physical space coordinates with one of the sets of image space coordinates a computer implemented method can be used to determine how to transform the head image including the one set of image space coordinates so that it is aligned with the physical orientation of the head. Furthermore, in like manner it is possible to align any of the N images with any other of the N images by comparing the two sets of image space coordinates in the two images to determine how to transform one head image so that it is aligned with the other head image.

The determination of the transformation necessary for alignment is referred to as "registration". Once this registration is determined, another computer implemented method can be used to calculate the position in image space of the ILD, no matter where the ILD is located in physical space. If, for example, the surgeon places the tip of the ILD somewhere within the brain, the image space coordinates of that physical location in the brain can be determined. Once the position of a point in image space is known, the intra-operative computer 54 can determine the slice of the volume image in which that point lies. The slice may then be displayed on a monitor 64 that is visible to the surgeon. Additionally, a cursor may be placed on that slice in the image displayed on the monitor at the position of the ILD. The effect is that the surgeon sees the image position on the monitor that corresponds to the physical position of the pointer of the ILD. This process of determining the ILD position in image space and displaying the correct slice with the correctly positioned cursor can be done so quickly (ten or more times per second) that the surgeon perceives the cursor on the image displayed on the monitor as moving through image space as the ILD pointer 60 moves through physical space in the operating room.

The result of the overall sequence of processes including image space localization, physical space localization, registration, transformation, and display, is a navigation system that enhances the surgeon's ability to perform surgery by allowing a display of a physical position in image space on a real-time basis.

The method according to the present invention may be implemented independently on each volume image. Thus, for example, if there were one CT image and two MR images, the method might first be applied to the CT image to determine the 3×M image space coordinates for the M markers in that image. Then, the method would be applied to one of the MR images to determine the 3×M image space coordinates for that image. Finally, the method would be applied to the second MR image to determine 3×M coordinates for that image. Each of these three processes would be performed independently. The order in which the images are processed is not critical in practicing the present invention. The method according to the present invention will be described below as being applied to one volume image.

A volume image consists of a set (typically 15 to 100) of rectangular arrays of integers. Each integer represents the intensity of the object averaged over a small three-dimensional rectangle called a "voxel." All voxels within a volume image preferably have the same size and shape, an image slice consisting of one rectangular array of voxels. The rectangular array is typically a 128 by 128, 256 by 256, or 512 by 512 square, but other dimensions are possible. When an image is displayed, each integer is mapped into a brightness level from black through gray to white which appears on a tiny, square, called a "pixel" on a computer display screen. The effect of viewing the complete two dimensional array of pixels is that one cross sectional slice is seen on the computer display screen 64. The volume is thus viewed on the display screen one slice at a time. The x and y coordinates may be used to specify positions within a slice, while the z coordinate may be used to measure positions in a direction perpendicular to the slice. Typically, $v_x=v_y$ and $v_x \leq v_z$, where $v_x$, $v_y$, and $v_z$ are the three dimensions of a voxel, the dimension $v_z$ being the slice thickness. It is preferred that $v_x=v_y$ and that $v_x \leq v_z$, and these values are assumed in the following description. It is noted that while the value of $v_z$ may vary from slice to slice, the value of $v_x$ and $v_y$ should be the same for all slices.

The method according to the present invention finds markers whose images are of a higher intensity than their surroundings. It is also tailored to find markers of a given size and shape. All of the marker may be visible in the image, or it may consist of both imageable and non-imageable parts. In one version the imageable part is a liquid, and the liquid is contained in a non-imageable container. It is the imageable part that is localized by the method according to the present invention, and the size and shape of this imageable part is important to the method. Henceforth, the term "marker" or "fiducial marker" refers to only the imageable portion of the fiducial marker assembly. Three pieces of geometrical information specify the size and shape of the marker adequately for the purposes of the present invention: (1) the radius of the largest sphere that can be inscribed within the marker, (2) the longest length of the marker (i.e., the greatest straight-line distance between any pair of points on the marker), and (3) the volume $V_m$ of the marker. A cylindrical marker as illustrated in FIG. 1 provides a useful example of these values, with the diameter of the circular face of the cylinder having a value d and its height having a value h. For this case the radius of the largest inscribable sphere equals the smaller of d/2 or h/2, the longest length of the marker is $\sqrt{d^2+h^2}$, and the volume $V_m$ is $\pi d^2 h/4$. Similar values can easily be determined for markers of different geometrical shapes or sizes other than cylindrical fiducial markers, such as, for example, spherical or cubic fiducial markers.

Figure 4:
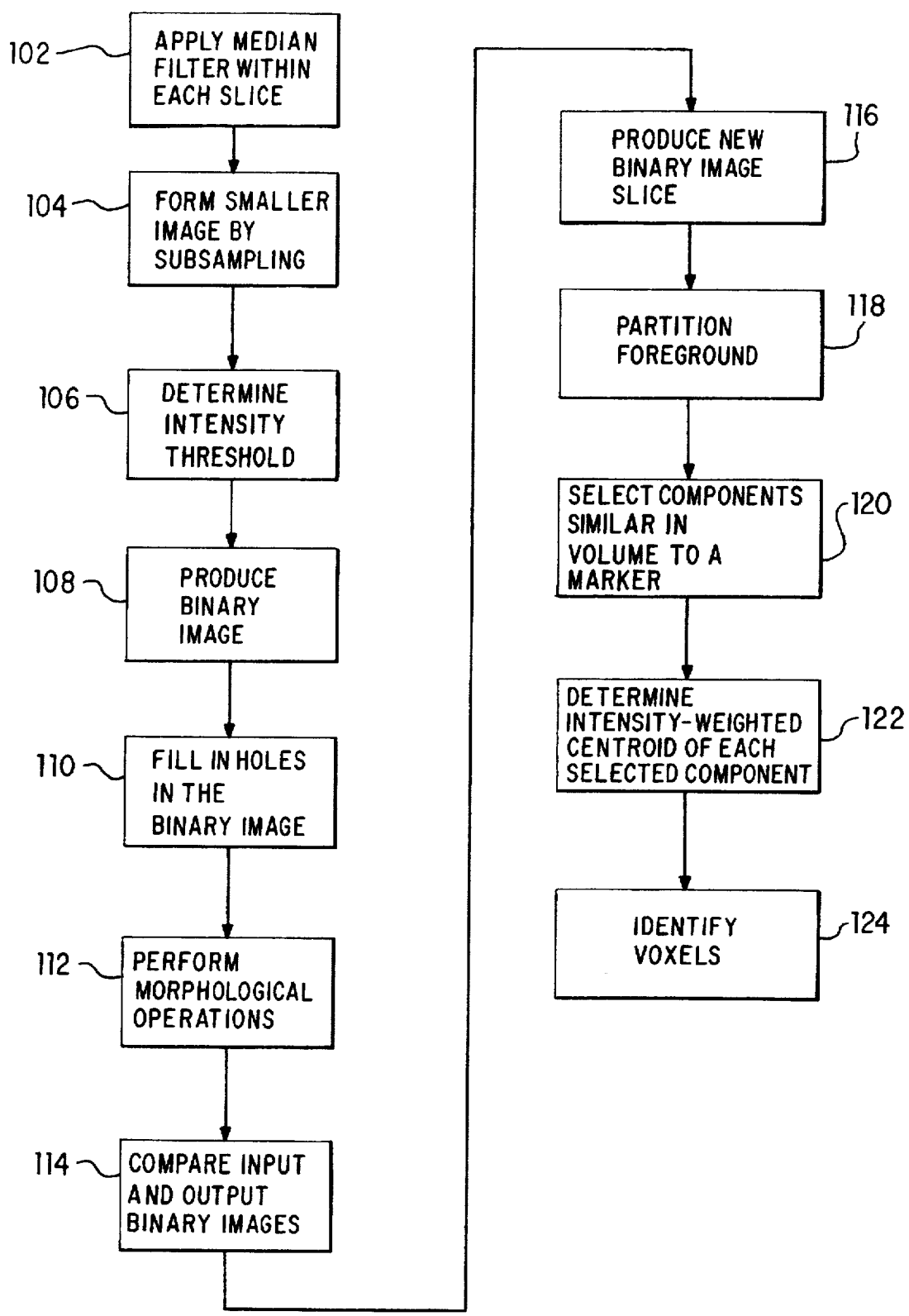
FIG. 4 is a flowchart illustrating a first portion of an embodiment of the present invention.
Figure 5:
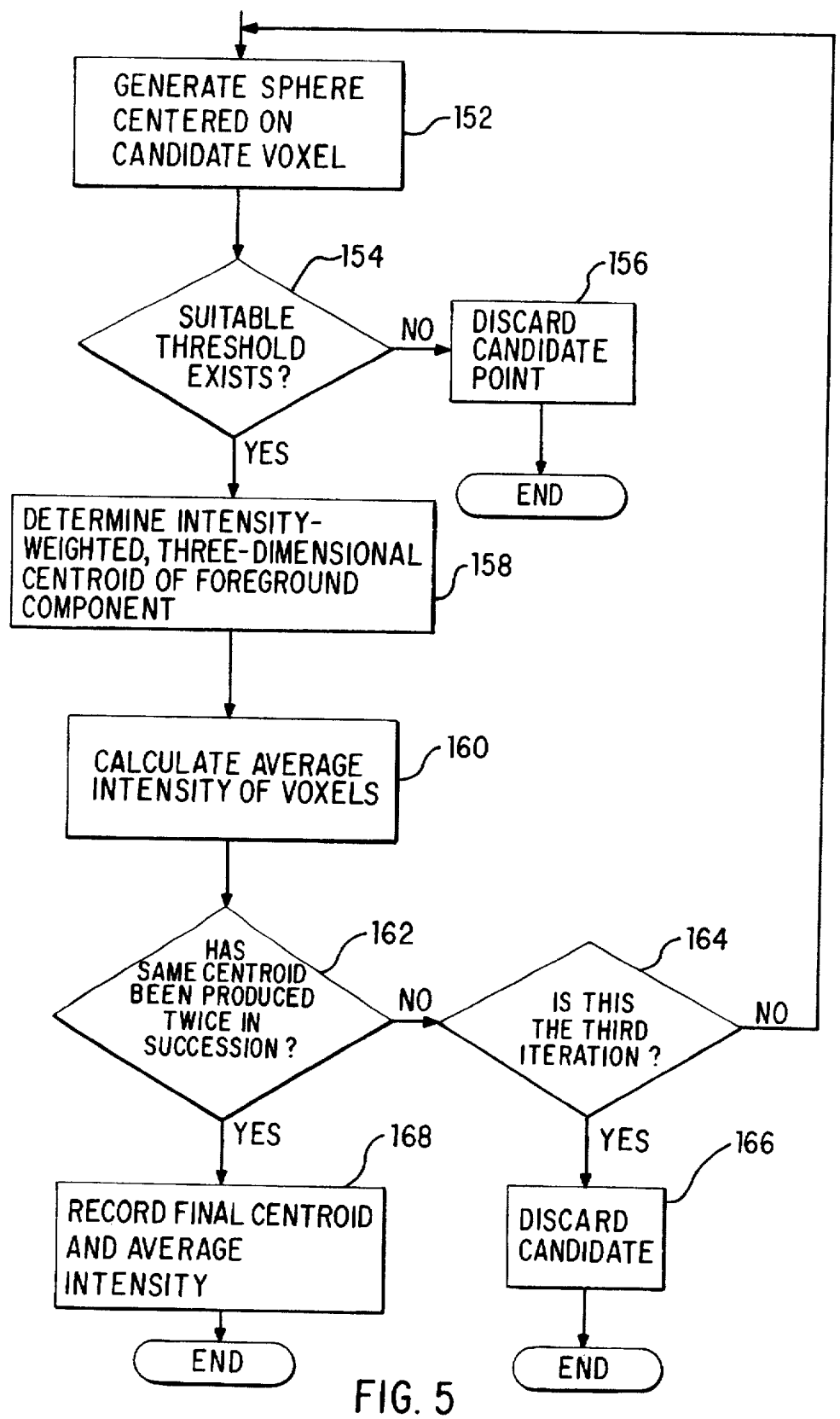
FIG. 5 is a flowchart illustrating a second portion of an embodiment of the present invention.

There are two parts to an embodiment of the method according to the present invention, including a first part illustrated by a flowchart diagram in FIG. 4 and a second part illustrated by a flowchart diagram in FIG. 5. The method illustrated in FIG. 4 finds "candidate voxels". Each candidate voxel lies within a bright region that might be the image of a marker. Minimal requirements are imposed by the method of FIG. 4 with the result that there are typically many more than M candidate points identified. If for example, M is four, the method of FIG. 4 might identify 100 candidates. The method of FIG. 5 selects from the candidates identified in the FIG. 4 method M candidate points that are most likely to lie within actual markers and determines a centroid for each marker. The method of FIG. 4 is designed so that it is unlikely to miss a true marker and the method of FIG. 5 is designed so that it is unlikely to accept a false marker.

INPUTS AND OUTPUTS

The first portion of the method receives the following as inputs:

the volume image of the head of a patient the number of image voxels in each dimension within a slice the number of slices the dimensions $v_x$, $v_y$ of a voxel the dimension $v_z$ of a voxel for each slice the dimensions d and h of a marker the intensity of an empty voxel The first part of the method produces as an output a set of candidate voxels in response to the inputs.

The second portion of the method receives the following as inputs:

the volume image of the head of a patient.

the number of image voxels in each dimension within a slice the number of slices the dimensions $v_x$, $v_y$ of a voxel the dimension $v_z$ of a voxel for each slice
the dimensions d and h of a marker
the intensity of an empty voxel
the set of candidate voxels produced by the first step
the number M of external markers present in the image The second part of the method produces as an output a list of M "fiducial points." Each fiducial point is a three dimensional position consisting of three coordinates $x_f$, $y_f$, $z_f$, that are likely to be the centroid of a marker. The list is ordered with the first member of the list being most likely to be a marker centroid and the last being the least likely.

The method illustrated in FIG. 4 operates on the entire volume image. In step 102 of the method of FIG. 4 if the image is an MR image, a two dimensional, three-by-three median filter is applied within each slice. First, for example, for each voxel in a slice a set of nine voxels in that slice is considered. The set of nine voxels includes the voxel under consideration and its "eight-connected neighbors". The eight-connected neighbors of a voxel under consideration lie in the same slice as the voxel and consist, for example, of the four voxels that each share a common side with the voxel and the four voxels that share only a common corner with the voxel. Second, the intensities of these nine voxels are ranked. The intensity that ranks fifth of these nine voxels is considered the median intensity of the set of nine voxels. Third, a new image provided as a result of the filtering includes a voxel at the position of the voxel under consideration which is assigned an intensity equal to the median intensity. This process is described, for example, at pages 191 and 192 of *Digital Image Processing* by Rafael C. Gonzalez and Richard E. Woods, Addison-Wesley Publishing Co., New York, 1992.

In step 104, a new smaller image is formed by subsampling. Subsampling produces a new image by, for example, the following procedure:

First, a subsampling rate is determined. The subsampling rate may be found as follows: the radius of the largest sphere that can be inscribed within a marker is divided by $v_x$. The fractional part of this number is dropped. The remaining integer is the subsampling rate.

Second, each voxel is indexed according to its position in the x and y directions, starting with zero in each direction. For example, the voxel in the upper left corner would be numbered, (0,0); the voxels to the right of this corner voxel would be numbered (1,0), (2,0), (3,0), (4,0), etc.; the voxels below the corner voxel would be numbered (0,1), (0,2), (0,3), (0,4), etc.

Third, a new image is formed in which all voxels are discarded except for those whose indices are each evenly divisible by the sampling rate. Thus, for example, if the rate were 1, no voxels would be discarded; if the rate were 2, voxels (1,0), (3,0), (0,1), (0,3), etc., would be discarded; if the rate were 3, voxels (1,0), (2,0), (4,0), (0,1), (0,2), (0,4), etc. would be discarded.

An intensity threshold is determined in step 106. For CT images the threshold preferably has a value that maximizes the between-group variance. The between-group variance is defined at, for example, page 22 of *Computer and Robot Vision*, Volume I, by Robert M. Haralick and Linda G. Shapiro, Addison-Wesley Publishing Co., New York, 1992.

If t is defined as the value of the threshold that divides the image into foreground (e.g., intensity greater than t) and background (e.g., intensity less than or equal to t), $q_1(t)$ is defined as the fraction of voxels that are classified as background and $q_2(t)$ is defined as the fraction of voxels that are classified as foreground, u is defined as the mean intensity of the entire image, $u_1(t)$ is defined as the mean intensity of the background voxels and $u_2(t)$ is defined as the mean intensity of the foreground voxels, the between-group variance is defined as:

$$q_1(t)|u_1(t)-u|^2+q_2(t)|u_2(t)-u|^2$$

Since $q_1(t)$, $q_2(t)$, $u_1(t)$, and $u_2(t)$ are functions of the threshold value t, it is possible to vary the between-group variance by varying the threshold value t.

For MR images the threshold is preferably computed as the mean of two independently determined thresholds. The first of these independent thresholds is the threshold that maximizes the between-group variance. The second is the threshold that minimizes the Kullback information value. The Kullback information value is defined at, for example, page 25 of *Computer and Robot Vision*, Volume 1, by Haralick and Shapiro.

If $v_1(t)$ is defined as the variance of the intensities of the background voxels and $v_2(t)$ is defined as the variance of the intensities of the foreground voxels, the Kullback information value is defined as:

$$(1+\log(2\pi)/2-q_1(t)\log(q_1(t))-q_2(t)\log(q_2(t))+[q_1(t)\log(v_1(t))+q_2(t)\log(v_2(t))]/2$$

Since $q_1(t)$, $q_2(t)$, $v_1(t)$, and $v_2(t)$ are functions of the threshold value t, it is possible to vary the Kullback information value by varying the threshold value t.

A binary image of foreground and background voxels is produced in step 108 based on the threshold determined in step 106. A voxel is a foreground voxel if its intensity is greater than or equal to the threshold intensity. Otherwise it is a background voxel. Foreground voxels are typically voxels that are part of the image of the patient's head and the markers.

If the original image is an MR image, spurious detail tends to appear in the binary image produced by the previous step 108. The spurious detail is composed of apparent holes in the head caused by regions that produce a weak signal, such as in the areas of cerebrospinal fluid, the skull and sinuses. Thus, if the original image is an MR image, these holes in the binary image are filled in step 110. In this step each slice is considered individually. A foreground component is a two-dimensionally connected set of foreground voxels. The holes are background regions completely enclosed within a slice by a single foreground component. These holes are found by identifying all sets of two-dimensionally connected background voxels that are not connected two-dimensionally to a background voxel in their slice that lies at one of the four corners of the image. Each such set is defined to be a hole that should be filled. The filling is accomplished by setting the voxels in each such set to a foreground voxel value.

Two successive binary, two-dimensional, morphological operations are performed on each slice in step 112. The operations taken together have the effect of removing small components and small protrusions on large components. In particular the operations are designed to be most likely to remove components and protrusions whose cross sections are smaller than or equal to the largest cross section of a marker. The operations are opening and dilation in that order. In each case, the structuring element is a square. For the opening operation the number of voxels on a side of the element is determined as follows: First the largest length of the marker is divided by $v_x$. Then, that number is rounded up to the nearest integer. The resulting integer is the desired number of voxels on a side of the opening element. For the dilation, the element is a single voxel.

Morphological operations are nonlinear operations on binary images that cause changes in the shape of the foreground objects. These operations are discussed in Chapters 1 and 2 of *An Introduction to Morphological Image Processing* by Edward R. Dougherty, SPIE Optical Engineering Press, Bellingham, Wash., 1992, which is incorporated herein by reference. The new shape of an object is determined by the manner in which a "structuring element" of a given shape fits within the object.

The basic fundamental morphological operation is erosion. The determination of the new image involves the following two steps: First, the structuring element is placed successively at all possible positions within the image. The position of the center pixel of the element is noted whenever the entire element lies within the foreground. Second, a new image is generated in which each noted position is set to foreground. All other position are set to background.

Another morphological operation is dilation. Dilation can be defined in terms of erosion. It consists of the following steps: First, the image is complemented, meaning that foreground voxels are set to background and background voxels are set to foreground. Second, the structuring element is rotated 180 degrees (this step has no effect on a square element). Third, erosion is effected. Fourth, the resulting image is complemented.

Another morphological operation mentioned above is called opening. It consists of an erosion, followed by a dilation, each performed with the same structuring element.

For each slice the binary image that was input to the previous step 112 and the binary image that was output by the previous step 112 are compared in step 114. A new binary image slice is produced in step 116 in which those voxels that were foreground voxels in the input image and were background voxels in the output image are set to the foreground value. The remaining voxels are set to a background value. The result is a binary image consisting only of the small components and protrusions that were removed in the previous step 112.

The foreground is partitioned into three-dimensionally connected components in step 118 for the entire volume image. The definition of connectedness can be varied. It is noted that including the eight two-dimensionally eight-connected neighbors within the slice plus the two voxels at the same x and y positions on the neighboring slices works well for both CT and MR images.

In step 120, components in the image that are sufficiently similar in volume to a marker are selected. The volume $V_c$ of a component is determined by counting its voxels and multiplying by the volume $V_v$ of one voxel, where $V_v = v_x v_y v_z$. The component is selected as a possible marker component if and only if the volume $V_c$ of the component falls within a range $[aV_m, bV_m]$, where the values of a and b depend on the characteristics of the imager (e.g., a CT or MR imager) and $V_m$ is the marker volume. Preferable values of a=0.1 and b=5.0 which work well for both CT and MR machines have been identified by the present inventors. A large range is chosen so that the method of FIG. 4 will have a low false negative rate. With these numbers for a and b only those components whose volume is too small by a factor of ten or too large by a factor of five will be dropped from consideration. Of course, other acceptable values may be used for a and b in practicing the method according to the present invention.

The intensity-weighted centroid of each selected component is found in step 122. This centroid consists of three values $x_c$, $y_c$, and $z_c$, each of which is calculated independently as follows:

$x_c = \Sigma(i-i_o)x/\Sigma(i-i_o)$ $y_c = \Sigma(i-i_o)y/\Sigma(i-i_o)$ $z_c = \Sigma(i-i_o)z/\Sigma(i-i_o)$ The sums are taken over all voxels in the component. The value i is the intensity of the voxel; $i_o$ is the intensity of an empty voxel; x, y, and z are the coordinates of the center of a voxel.

The voxels which contain the points $x_c$, $y_c$, $z_c$ are identified in step 124. The voxels identified in step 124 are the candidate voxels provided by the method of FIG. 4.

The second part of the present invention is illustrated in FIG. 5 and operates on a small region of the original image around each candidate voxel. The method of FIG. 5 takes the steps described below for each candidate voxel identified in the method of FIG. 4.

Step 152 of FIG. 5 generates a sphere centered on the candidate voxel having a radius R equivalent to the largest length of a marker being localized. For example, in implementing the method of the present invention in which cylindrical fiducial markers are localized, $R = \sqrt{d^2 + h^2}$.

Step 154 determines whether a suitable threshold exists for the candidate. This determination can be made by checking each intensity value in the available range of intensities. Alternatively, a more efficient search strategy can be adopted such as a binary search strategy. In either case a suitable threshold is defined as follows: for a given threshold the set of foreground voxels that are three-dimensionally connected to the candidate voxel are identified. The threshold is suitable if the size and shape of this foreground component is sufficiently similar to that of a marker. There are two rules that determine whether the size and shape of the foreground component are sufficiently similar:

(a) The distance from the center of the candidate voxel to the center of the most distant voxel of the foreground component must be less than or equal to the largest length of a marker.

(b) The volume $V_c$ of the component, calculated by multiplying $V_v$ times the number of voxels in the component, must be within the range $[V_l, V_h]$ where $V_l$ is preferably in a range of values between $V_v$ and $V_m$, and $V_h$ is preferably in a range of values between $V_m$ and $10V_m$. The present inventors have identified that the range $[0.6V_m, 3.0V_m]$ works well for both CT and MR images.

The preferred implementation of performing a suitable threshold according to the above-mentioned rules is performed according to a knowledge based search as follows. S(t) is defined as the set of voxels in this region whose intensity i is greater than the threshold t and which are connected recursively (in 3D) to the starting point. V(t) is defined as the volume of the set of voxels S(t), and $V_h$ is the maximum volume and $V_l$ is the minimum volume that are allowed for a marker image. The method according to a preferred embodiment of the present invention first searches for the smallest t such that no voxel included in the set of voxels S(t) is farther than R from the starting point. If $V(t) > V_h$, t is increased until $V(t) = V_h$. If $V(t) < V_l$ the segmentation fails and the candidate voxel is discarded.

If step 154 determines that no such threshold exists, the candidate point is discarded in step 156. If there are two or more suitable thresholds, the smallest one is chosen as the threshold value.

If the threshold does exist, the following steps are taken:
(a) The intensity-weighted, three-dimensional centroid of the foreground component is calculated in step 158 using the intensities of the voxels in the original image. This centroid consists of three values $x_f$, $y_f$, and $z_f$, each of which is calculated independently as follows:

$$x_f = \Sigma(i-i_o) x / \Sigma(i-i_o)$$
$$y_f = \Sigma(i-i_o) y / \Sigma(i-i_o)$$
$$z_f = \Sigma(i-i_o) z / \Sigma(i-i_o)$$

(b) The average intensity of the voxels in the foreground component is calculated in step 160 using the voxel intensities in the original image.

The voxel that contains the centroid $x_f$, $y_f$, $z_f$ is eventually fed back to step 152 as a candidate marker. If this second centroid differs from the first, it is fed back to step 152 and a third centroid is produced. This is accomplished as follows. If a determination is made in step 162 that the same centroid has not been produced twice in succession by the iteration, step 164 determines whether or not this is the third iteration for this candidate voxel. If the third iteration has occurred for the candidate voxel, the candidate is discarded in step 166. Otherwise the final centroid and its associated average intensity is recorded in step 168. The steps of FIG. 5 are then repeated for each of the other candidate voxels identified by the method illustrated in FIG. 4.

Figure 6:
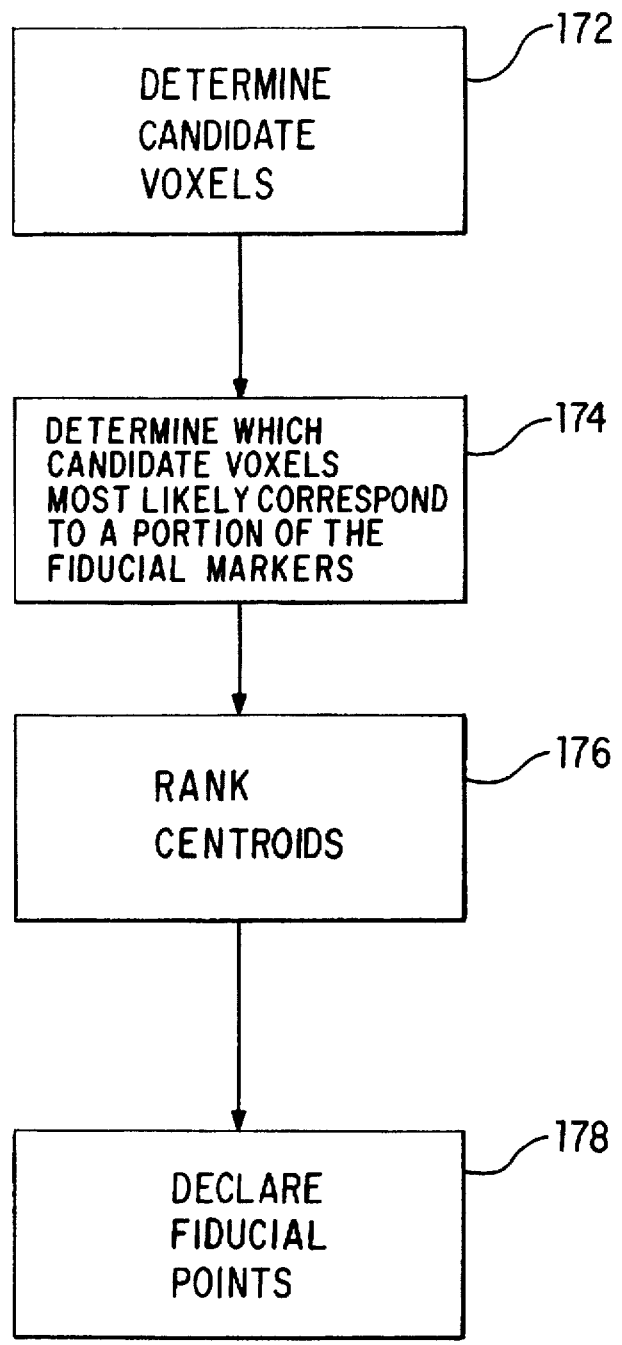
FIG. 6 is a flowchart illustrating an embodiment of the localization technique of the present invention.

FIG. 6 is a flowchart illustrating an embodiment of the localization method according to the present invention. Candidate voxels which may be included in candidate fiducial markers are determined in step 172, which may be performed according to the steps illustrated in FIG. 4. A region around each of the candidate voxels may be examined in step 174 to determine which of the candidate voxels identified in step 172 most likely correspond to the fiducial markers to be localized. Step 174 may be accomplished, for example, by performing the method illustrated in FIG. 5 for each of the candidate voxels determined in step 172. The centroids $x_f$, $y_f$, $z_f$ of the most likely candidate voxels determined in step 174 are ranked in step 176 according to the average intensity of their components. In step 178, the M points with the highest intensities are declared to be fiducial points, which are output in order by rank. A candidate with a higher intensity is considered to be a more likely fiducial point. The M most likely candidates are declared as the fiducial points, where M is the number of fiducial markers being localized. However, a different number of most likely candidates may be declared in step 178.

The method of the present invention was developed on a set of clinical scans from six patients –6 CT volumes, 12 MR T1-weighted, 12 MR PD-weighted, and 12 MR T2-weighted volumes, each with 4 mm slice thickness. Each patient had four attached cylindrical markers with h=5 mm and d=7 mm. There were no false positives or false negatives for the CT scans. For the MR scans the false positive rate and the false negative rate were equal to 1.4%. To evaluate the accuracy of the fiducial points, MR-CT registration was performed using geometrical correction for the MR images. The fiducial registration accuracies averaged 0.4 mm and were better than 0.6 mm on each of the eighteen image pairs.

While the present invention has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims.

What is claimed is:

1. A method for automatically localizing a predetermined number M of fiducial markers in at least one image volume, comprising steps of:

searching the at least one image volume for candidate markers, said markers including a number of three-dimensional connected voxels having similar intensities and being within a predetermined size range;

representing each of said candidate markers by a candidate voxel containing the centroid of the candidate marker; and examining a three-dimensional region in the at least one image volume around each of the candidate voxels and determining which of said candidate markers represented by said candidate voxels most likely correspond to said fiducial markers in said at least one image volume, and including for each of said candidate voxels:

determining whether a size and shape of a set of foreground voxels connected to said candidate voxel is similar to a foreground component of a fiducial marker;

discarding the candidate voxel if the size and shape are not determined to be similar;

determining a centroid of the set of foreground voxels;

repeating said determining steps until a same centroid has been determined twice in succession;

discarding the candidate voxel if the determining steps are implemented a predetermined number of times; and if a same centroid has been determined twice in succession, recording said same centroid as a final centroid and recording a corresponding intensity of said final centroid.

2. The method of claim 1, wherein said predetermined number of times is three.

3. The method of claim 1, further comprising a step of ranking the recorded final centroids of each of said candidate voxels according to their corresponding recorded intensities.

4. A method for automatically localizing three-dimensional centroids of a predetermined number M of fiducial markers in at least one image volume, comprising steps of:

searching the at least one image volume for candidate markers, said candidate markers including a number of three-dimensional connected voxels having similar intensities and being within a predetermined size range and representing each of said candidate markers by a candidate voxel containing the centroid of the candidate marker, including:

applying a median filter within each of a plurality of slices of the at least one image volume;

forming a new smaller image volume for each slice by subsampling;

determining an intensity threshold value;

producing a binary image from said new smaller image of foreground and background voxels in response to said intensity threshold value;

filling in any holes in the binary image;

removing small components and small protrusions on large components appearing in the binary image;

selecting components in the removed binary image which are most similar to a fiducial marker, said number of components being larger than said predetermined number M; and providing said selected components as the candidate voxels;

examining a three-dimensional region in the at least one image volume around each of the candidate voxels and determining which of said candidate markers represented by said candidate voxels most likely correspond to said fiducial markers in said at least one image volume including for each of said candidate voxels:

determining whether a size and shape of a set of foreground voxels connected to said candidate voxel is similar to a foreground component of a marker;

discarding the candidate voxel if the size and shape are not determined to be similar;

determining a centroid of the set of foreground voxels;

repeating said determining steps until a same centroid has been determined twice in succession;

discarding the candidate voxel if the determining steps are implemented a predetermined number of times; and if a same centroid has been determined twice in succession, recording said same centroid as a final centroid and recording a corresponding intensity of said final centroid.

5. The method of claim 4, wherein said predetermined number of times is three.

6. The method of claim 4, further comprising a step of ranking the recorded final centroids of each of said candidate voxels according to their corresponding recorded intensities.

* * * * *